United States Patent [19]

Enders et al.

[11] 4,150,107

[45] Apr. 17, 1979

[54] ANTIGEN FROM SCHISTOSOMES AND PROCESS FOR OBTAINING SAME

[75] Inventors: Burkhard Enders, Marburg-Marbach; Günter Henke, Stadt Allendorf, both of Fed. Rep. of Germany

[73] Assignee: Behringwerke Aktiengesellschaft, Marburg, Lahn, Fed. Rep. of Germany

[21] Appl. No.: 840,175

[22] Filed: Oct. 7, 1977

Related U.S. Application Data

[63] Continuation of Ser. No. 572,086, Apr. 28, 1976, abandoned.

[30] Foreign Application Priority Data

Apr. 29, 1974 [DE] Fed. Rep. of Germany ....... 2420706

[51] Int. Cl.$^2$ ............. A61K 29/00; A61K 39/00; A61K 41/00; G01N 33/16
[52] U.S. Cl. ...................... 424/9; 23/230 B; 260/112 R; 260/112 B; 424/12; 424/85; 424/88; 424/177
[58] Field of Search ............ 23/230 B; 424/8, 9, 424/12, 85, 88, 93, 177; 260/112 R, 112 B

[56] References Cited

PUBLICATIONS

Sawada, Japan Exp. Med., vol. 39, 1969, pp. 339-345.
Sato, Japan J. Exp. Med., vol. 39, 1969, pp. 355-358.
Green, PSEBM, vol. 141, 1972, pp. 291-294.
Bueding, PSEBM, vol. 64, 1947, pp. 111-113.
Von Brand, Biochem. of Parasites, Acd. Press, NY, 1966, pp. 19-27, 90.
Senft, J. of Parasitology, vol. 48, 1962, pp. 551-553.
Enders, Rev. de Inst. Med. Trop. Sao Paulo, vol. 16, No. 6, Nov.-Dec., 1974, pp. 305-316.
Higashi, Life Sci, vol. 13, No. 9, 1973, pp. 1211-1220.
Enders et al., J. Parasitology, vol. 56, 1970, p. 420 Ab. No. 754.
Hohorst et al., Bade Dermatitis, De Gelben Hefte, vol. 1, 1972, pp. 8-13.

Primary Examiner—Anna P. Fagelson
Attorney, Agent, or Firm—Curtis, Morris & Safford

[57] ABSTRACT

The invention relates to a process for obtaining antigens from living adult schistosomes, wherein schistosomes are kept alive for 12 to 96 hours in a sterile physiologically tolerable salt solution, subsequently isolated and extracted with an aqueous medium, as well as diagnostics for bilharziasis infections containing such antigens or corresponding antibodies and their use for the proof of bilharziasis in vivo and in vitro.

9 Claims, No Drawings

ANTIGEN FROM SCHISTOSOMES AND PROCESS FOR OBTAINING SAME

This is a continuation, of application Ser. No. 572,086, filed Apr. 28, 1976, now abandoned.

The invention relates to a process for obtaining antigens from living adult schistosomes, diagnostics for bilharziasis infections containing such antigens or corresponding antibodies and their use for the proof of bilharziasis in vivo and in vitro.

Bilharziasis is a disease provoked by parasites of the genus Schistosoma. It is estimated that approximately 200 million persons, especially in Asia, Africa, South and Central America are infected by Schistosome species pathogenic to human beings, especially Schistosoma mansoni, Schistosoma haematobium and Schistosoma japonicum.

For about 50 years, serological methods have been used for the diagnosis of the bilharziasis, which, as compared to parasitological procedures, have considerable advantages due to their simple execution. The specifity of these test processes largely depends on the quality of the antigen material used therefor.

It is known that patients infected by bilharziasis show in an early stage of the disease, a specific sensitivity of the skin which is attributed to existing antibodies against the pathogen and may be provoked with corresponding antigens. An intradermal injection of a schistosoma extract leads within a few minutes to a reddening and induration (urtication) of the injected cutaneous area.

The antibodies are detectable in vitro with known test processes if suitable antigens are used.

As starting material for obtaining the antigens there are employed, inter alia, certain developing stages of the life cycle of schistosomes, preferably adult schistosomes which are brought to development in a host animal, the most frequently in rodents. The organisms are obtained with a perfusion technique described by Pellegrino and Siqueira, Rev. Bras. Mular. 8, 589 (1956), also discussed by Kagan et al. in the review article entitled "A Critical Review of Immunological Methods for the Diagnosis of Bilharziasis", Bull. Wld. Hlth. Org. 25, 611-674 (1961). The schistosomes to be obtained from the perfusion solution are washed with an isotonic sodium chloride solution and then used either directly for the preparation of antigen or dried and preserved in ampules until it is needed.

Antigens used for diagnosis are prepared either by extraction of the dried worms with an isotonic sodium chloride solution (sodium chloride extract) or by extraction with the aid of the solution according to Coca (Coca extract) or according to the proposal of Melcher by delipidization of the schistosomes with petroleum ether and subsequent extraction with borate buffer and a purification by acid precipitation, whereafter the acid-soluble fraction is obtained as a so-called Melcher antigen. Several attempts have been made to further purify the antigens obtained according to this process. In the skin test reactive fractions have also been obtained. It could also been shown that the active part of the skin test antigen is not to be limited to the pure fractions. It could, rather, be determined that the reactivity of the antigen is to be brought into correlation with the nitrogen content thereof. In this context it is always required that unspecific reactions, which can be caused by incorporation of constituents specific to the host into the organism of the schistosomes are eliminated.

It has now been found that the schistosomes obtained by perfusion from rodent blood may be freed from a large part of material specific to the host by keeping the schistosomes for several hours in a suitable protein-free salt medium, and that these previously purified schistosomes provide somatic antigens having an increased specifity.

Thus, the present invention relates to a process for preparing antigens from living adult schistosomes wherein schistosomes obtained from infected animals are kept in a living state for 12 to 96 hours in 10 to 100 times their volume of a sterile protein-free and nitrogen-free, physiologically tolerable aqueous salt solution at 10° C.–40° C. and then isolated and extracted with an aqueous medium.

As salt solutions in which the schistosomes after being obtained are kept alive for some time, all physiologically tolerable aqueous salt solutions are suitable, the osmolarity of which is about 200 to 450 milliosmols/l. Besides a physiological sodium chloride solution there may be mentioned the known nutrient solutions, for example according to Locke, Tyrode or Ringer. Additives of about 0.5% of glucose and/or about 1% of asparagine, which are known to be capable of keeping alive schistosomes in nutrient solutions for 2 to 12 days, are also advantageous in the process of the invention.

A particularly advantageous variant is that the schistosomes obtained by perfusion are kept in about 50 times of their volume of an aqueous solution containing NaCl, KCl, $MgSO_4$, glucose, $NaHCO_3$, $NaHPO_4$ and $CaCl_2$ with a concentration of 200 to 450 milliosmols/l at 35°–40° C., with the proviso that at least the half of the osmolarity of the solution is due to the content of sodium chloride and that the other constituents contribute in each case 2 to 50 milliosmols/l to the content of dissociated substance in the solution. It is known that for the preparation of an optically clear solution the salts indicated cannot be added to the solvent water in any mixture ratio desired. For example the aqueous solution may have the following composition:

- 0.120 mol/l corresponding to 240 milliosmols/l of NaCl
- 0.004 mol/l corresponding to 8 milliosmols/l of KCl
- 0.0007 mol/l corresponding to 2 milliosmols/l of $MgSO_4$
- 0.0055 mol/l corresponding to 5 milliosmols/l of glucose
- 0.018 mol/l corresponding to 36 milliosmol/l of $NaHCO_3$
- 0.0035 mol/l corresponding to 10 milliosmol/l of $Na_2HPO_4$
- 0.001 mol/l corresponding to 3 milliosmol/l of $CaCl_2$ It has proved advantageous to change the solution several times at intervals of some hours, for example to change the solution every eight hours while keeping the worms for 24 hours.

It has not been known hitherto that schistosomes during the incubation time are able to set free the nutrient substances taken up by the intestine in the corresponding media and that, in this way, a considerable purifying effect results in the preparation of the somatic antigens. That is to say, it can be shown that the moist weight of the schistosomes obtained by perfusion from a host animal decreases by 10 to 30% by the incubation according to the invention. This decrease of the weight of the worm leads to a considerably purer starting material for the preparation of the somatic antigens.

Whereas non incubated schistosomes can only be treated by very mild measures in extraction processes for obtaining the antigens, the increased purity of the starting material permits the use of more intense shearing and cavitation forces, for example supersonics, and then leads to a higher yield of specific antigen material.

The schistosomes serving as starting material for the process of the invention are obtained in known manner, for example with the aid of the perfusion technique from the blood of infected animals. Suitable animals are for example swine, or preferably rodents such as rabbits, guinea pigs, golden hamsters or especially rats or mice. It is expedient to infect the animals artificially in order to obtain the schistosomes, but there may also be used naturally infected animals, but it must be accepted that a less homogeneous starting material is obtained.

The schistosomes are collected, expediently on a sieve having the suitable mesh size and washed again, for example on this sieve or by decanting. The washing solution is an aqueous salt solution isotonic with regard to the organisms, expediently a sodium chloride solution.

The schistosomes thus prepared are kept alive in a salt solution in the manner described.

Then the incubated schistosomes are separated from the salt solution by decanting or sieving and, if desired, washed again with isotonic salt solution or with pure water.

The subsequent extraction is carried out with the above-described and known media as extracting agents, which have hitherto been used for the extraction of schistosomes not pretreated according to the invention but which provide a considerably improved extract with the schistosomes of the invention.

If desired, the schistosomes isolated from the salt solution may be freeze-dried before the extraction and/or delipidized with at least 50 times their dry weight of lipid solvents such as diethyl ether. Before or during the extraction the use of shearing or cavitation forces may be advantageous, for example treatment with a rapid stirrer or with supersonics or a simple mechanical triturating. After the extraction, the aqueous extract obtained may, if desired, be subjected to further purification such as dialysis or chromatography.

The purified product may be standardized according to the requirements of the diagnostic test systems for the proof of bilharziasis.

For the intradermal test, it has proved advantageous, as a result of extensive field tests, to carry out a determination of nitrogen in the antigen material and to adjust the solution of the somatic antigens to a final concentration of 0.03 mg of nitrogen per ml with the aid of a physiologically tolerable salt solution.

The invention further relates to antigens which may be prepared from schistosomes obtained from infected animals, after they have been kept alive at 10°–40° C. for 12 to 96 hours in 10 to 100 times their volume in a chemically defined sterile isotonic salt medium free from protein and nitrogen.

Standardized antigens prepared according to the invention and calculated on the amount of nitrogen obtained from schistosomes permit epidemiological examinations with persons infected by bilharziasis. The intradermal injection of 0.05 ml of the antigen solution provokes urtication in the skin at the place of injection; urtication of a surface of more than 1 $cm^2$ 15 minutes after the injection is considered as a reliable symptom of the existence of antibodies of schistosomes. On account of serological cross reactions with schistosomes pathogenic to animals, for example Trichobilharzia spp. and Ocellata spp. which invade the humans as substitute host, the above-mentioned antigen may be used diagnostically for demonstrating the contact established with the corresponding schistosoma stages.

However, the antigens of the invention prove to be suitable for carrying out the hemagglutination test, as described by Kagan in 1955, for the diagnosis of bilharziasis [cf. Kagan et al., Bull. Wld. Hlth. Org. 25 611–674 (1961)].

The antigen obtained according to the invention may also be used for the complement fixing reaction which has been described as a diagnostic process for the proof of schistosomes Kagan et. al., op. cit.

Besides the methods mentioned, the antigens of the invention may be used for a series of further serological test processes as an antigen in the diagnosis of bilharziasis. They may also be used to obtain antiserum which may be obtained by immunization of suitable test animals with the schistosoma antigen. In this context sera may be obtained, the behavior of which in immunological systems is similar to that of the sera which may be taken from patients infected by bilharziasis.

Thus, further objects of the invention are diagnostic agents containing somatic antigens previously purified or obtained according to the invention and the use of the diagnostic agents for the demonstration of bilharziasis.

The following Example illustrates the invention.

EXAMPLE 35 g of schistosomes weighed out in a moist state obtained with a perfusion technique from the blood vessels of the mesenterium of experimentally infected mice were washed several times under sterile conditions on a sieve having a mesh size of 0.5 mm with 100 ml portions of a sterile isotonic sodium chloride solution. The worms freed in this way from adhering foreign substances were added to 500 ml of a solution, having the following composition and filtered under sterile conditions

|  | g/l |
|---|---|
| NaCl | 7.4 |
| KCl | 0.75 |
| $CaCl_2$ | 0.55 |
| $MgCl_2 \cdot 6H_2O$ | 0.2 |
| $Na_2HPO_4 \cdot 2H_2O$ | 2.7 |
| $NaHCO_3$ | 0.84 |
| Na-citrate | 2.9 |
| Glucose | 3.6 |
| pH-value | 8.3, | and kept for 24 hours at 37° C. After 8 hour intervals the solution was replaced by another 500 liters.

Then the worms were washed on a sieve with 100 ml of a sterile isotonic sodium chloride solution, suspended in about 100 ml of sterile distilled water and dried. 6.25 g of dry schistosomes were obtained.

To obtain the somatic antigens from the schistosomes, the dried worm material was finely pulverized in a mortar and subsequently homogenized portionwise in a tissue homogenizer according to Potter (fabricated by Messrs. B. Braun, Melsungen) with 950 ml of diethyl ether. The homogenization vessel was cooled from the outside with a mixture of methanol and solid carbon dioxide. The constituents insoluble in ether were centrifuged in a cooling centrifuge protected against explosion at −10° C. The excess was rejected and the residue was freed from the remaining ether under reduced pressure in an exsiccator. The total amount of the dry substances was suspended in 625 ml of a sodium chloride solution (pH 7.4) buffered with sodium borate, consisting of 6.202 g of $H_3BO_3$, 50 ml of 1N NaOH, 2.925 g of NaCl, and 46.5 ml of 1N HCl filled up to 1000 ml with distilled water, and divided homogeneously in the solution with the tissue homogenizer mentioned. Then the homogenized product was subjected for 10 minutes to a treatment with supersonics at 0.6 A, 220 V (device constructed by Scholler-Schall). Then the product was centrifuged for one hour at 30,000 g, the sediment was rejected and the supernatant containing the somatic antigen was dialysed for 10 hours against a 10 fold volume of the borate-buffered sodium hydroxide solution. The somatic antigens obtained in the inner dialysate may be used for the preparation of diagnostics for bilharziasis infections.

If desired, the antigens could be further purified by suitable chromatographic measures and decomposed into individual components for special tests.

The determination of the biological activity of the somatic antigens obtained was effected on guinea pigs, to which the serum of bilharziasis patients with sure parasitological results had been injected, by the proof of cutaneous passive anaphylaxis.

When, 48 hours after the administration of the serum, the antigen prepared according to the above Example was administered intracutaneously, in a dilution of 1:50, to the animals sensitized with these sera of patients, and simultaneously 1.2 ml of a 0.12% solution of Evans Blue was administered intraveneously, the place of injection showed a blue mark.

The serological activity was determined by titration by means of the passive hemagglutination technique according to Kagan (1955), whereby, as a serum standard, selected sera of patients infected by bilharziasis were used [cf. Kagan et al., Bull. Wld. Hlth. Org. 25, 611-674 (1961)].

What we claim is:

1. In the method of making an antigen which comprises extracting schistosomes with an aqueous medium, the improvement wherein said schistosomes are stored, prior to said extraction, for 12 to 96 hours at a temperature between 10° C. and 40° C. in 10- to 100-fold, by volume of said schistosomes, of a sterile, physiologically tolerable, protein-free, and nitrogen-free aqueous salt solution.

2. A method as in claim 1 wherein said aqueous salt solution contains sodium chloride, potassium chloride, magnesium sulfate, glucose, sodium bicarbonate, disodium phosphate, and potassium chloride in a total concentration of 200 to 450 milliosmols/liter, and wherein at least half the osmolarity of the solution is due to the sodium chloride content and the other constituents in each case contribute from 2 to 50 milliosmols/liter.

3. A method as in claim 2 wherein said schistosomes are freeze-dried after storage and prior to said extraction.

4. A method as in claim 2 wherein said schistosomes are treated with a lipid solvent after storage and prior to said extraction.

5. A method as in claim 2 wherein said schistosomes are dialyzed after storage and prior to said extraction.

6. A method as in claim 2 wherein said schistosomes are subjected to shearing or cavitation forces after storage and prior to said extraction.

7. A method as in claim 2 wherein said schistosomes are subjected to shearing or cavitation forces during said extraction.

8. An antigen prepared by the method of claim 2.

9. A diagnostic agent comprising an antigen as in claim 8 diluted with a physiologically tolerable salt solution to give a final concentration of 0.03 mg of nitrogen per milliliter.

* * * * *

UNITED STATES PATENT AND TRADEMARK OFFICE
CERTIFICATE OF CORRECTION

PATENT NO. : 4,150,107
DATED : April 17, 1979
INVENTOR(S) : Enders et al.

It is certified that error appears in the above-identified patent and that said Letters Patent are hereby corrected as shown below:

In the Heading, Item [63] and in column 1, line 6, the date "Apr. 28, 1976" should be --Apr. 28, 1975--.

Signed and Sealed this

Twenty-first Day of August 1979

[SEAL]

Attest:

LUTRELLE F. PARKER

Attesting Officer    Acting Commissioner of Patents and Trademarks